(12) United States Patent
Kaletin et al.

(10) Patent No.: US 7,922,347 B2
(45) Date of Patent: Apr. 12, 2011

(54) SURGICAL LIGHT PROVIDED WITH A LIGHT EMISSION CONTROL

(75) Inventors: Andrei A. Kaletin, Ekaterinburg (RU);
Olga M. Rosichina, Ekaterinburg (RU);
Dmitry V. Tsepelev, Ekaterinburg (RU);
Nikolai A. Osipov, Moscow obl. (RU);
Nikolai F. Vershinin, Moscow obl. (RU)

(73) Assignee: Zao Zavod Ema, Ekaterinburg (RU)

( * ) Notice: Subject to any disclaimer, the term of this patent is extended or adjusted under 35 U.S.C. 154(b) by 0 days.

(21) Appl. No.: 12/175,754

(22) Filed: Jul. 18, 2008

(65) Prior Publication Data
US 2008/0273317 A1  Nov. 6, 2008

Related U.S. Application Data

(63) Continuation of application No. PCT/RU2006/000021, filed on Jan. 24, 2006.

(51) Int. Cl.
*A61G 13/00*  (2006.01)
(52) U.S. Cl. ........... 362/33; 362/800; 362/572; 362/232
(58) Field of Classification Search .................... 362/33, 362/800, 572, 232; 600/249
See application file for complete search history.

(56) References Cited

U.S. PATENT DOCUMENTS

| 6,033,087 | A * | 3/2000 | Shozo et al. | 362/244 |
|---|---|---|---|---|
| 2002/0048170 | A1 * | 4/2002 | Momot et al. | 362/244 |
| 2003/0185009 | A1 * | 10/2003 | Walters | 362/276 |
| 2005/0195599 | A1 | 9/2005 | Marka | |

FOREIGN PATENT DOCUMENTS

| EP | 1568935 A1 | 8/2005 |
|---|---|---|
| JP | 2004200102 A | 7/2004 |
| RU | 2123633 C1 | 12/1998 |
| RU | 2149309 C1 | 5/2000 |
| RU | 2151473 C1 | 6/2000 |
| RU | 2153623 C1 | 7/2000 |
| RU | 2158876 C1 | 11/2000 |
| RU | 2202731 C2 | 4/2003 |
| RU | 2227245 C2 | 4/2004 |
| RU | 2235942 C2 | 9/2004 |
| RU | 2244870 C2 | 1/2005 |
| RU | 2248499 C2 | 3/2005 |

OTHER PUBLICATIONS

International Search Report, mailed Oct. 19, 2006, from International Application No. PCT/RU2006/000021, filed Jan. 24, 2006.

* cited by examiner

*Primary Examiner* — Sandra L O Shea
*Assistant Examiner* — Jessica L McMillan
(74) *Attorney, Agent, or Firm* — Houston Eliseeva, LLP

(57) ABSTRACT

The inventive surgical light comprises a body provided with main light-emitting diodes and additional light-emitting diodes arranged therebetween, which are spaced on said body and fixed thereto, wherein said additional light-emitting diodes are grouped and are characterised in that the spatial orientation thereof differs from the spatial orientation of the main light-emitting diodes. A light field control device comprises a control unit to which the groups of light-emitting diodes are connected by means of adjusters each of which is connected to a power supply unit. The main light-emitting diodes are fixed to the light body in such a way that the optical axes thereof cross the light axis in the center of a light spot. The additional light-emitting diodes are fixed to the light body in such a way that the optical axes thereof form a concentric light spot in the form of a ring around the main light spot.

2 Claims, 3 Drawing Sheets

SURGICAL LIGHT PROVIDED WITH A LIGHT EMISSION CONTROL

RELATED APPLICATIONS

This application is a Continuation of PCT application serial number PCT/RU2006/000021 filed on Jan. 24, 2006, which is incorporated herein by reference in its entirety.

FIELD OF THE INVENTION

This invention relates to medical technology, and more particularly to a lighting device wherein illumination is provided by a plurality of light-emitting diodes with light emission control.

BACKGROUND OF THE INVENTION

Since light-emitting diodes came into practice, lighting equipment using lamps composed of light-emitting diodes has displayed special advantages over the existing fluorescent lamps, incandescent lamps and the like, these advantages being their longer service life and lower energy consumption.

Lighting devices with light-emitting diodes (LEDs) used as searchlights or traffic lights are described in detail in the RF patents such as No. 2123633, No. 2151473, No. 2153623, No. 2202731, No. 2227245, No. 2244870, No. 2248499, etc. The purpose thereof is to illuminate remote objects, to be used in circular scanning systems and lighting devices which do not require the creation of a maximum level of illumination within a working zone or maintaining a constant diameter of the light field.

However, until now LEDs have not found broad use in surgical lighting devices, which are required to ensure a shadowless effect and a high illuminating efficiency through high illuminance and uniform distribution of luminous flux across the working zone. The luminous flux in surgical lighting devices is created by combining the luminous fluxes emitted by individual light-optical modules, which occurs at a distance of 0.7 m to 1.4 m from the body. Inside the working zone, a maximum level of illumination is created and a constant diameter of the light field is maintained. Moreover, the possibility of adjusting the diameter of the light field should be provided for. To this end, surgical lights are provided with light field control devices which represent, in general, rotary mechanical devices.

Known is a surgical light with a light field adjusting mechanism made in the form of a rotary mirror reflecting the light beam from a source of light (Lighting device type BH-500 manufactured by FAMED, Poland).

This known lighting device is provided with a light field adjusting mechanism which is not sufficiently effective because of low synchronization of rays, use of extra reflecting surface, and also it has large dimensions.

Known is a surgical lighting device in which the adjustment of the illumination system is performed by moving the lamp relative to the reflector (surgical light CH-6; certificate 66-00-00ПС).

The known lighting device may only adjust the size of a light spot featuring small depth, this lighting device also has large overall dimensions.

Also known is a surgical light with light emission control comprising light optical elements in the form of halogen lamps secured in the body and a light field adjustment mechanism, including a supporting rod mounted on the main axis of the lighting system, said supporting rod having a split spherical joint with six degrees of freedom in the upper part thereof, a means for rotating the light-optical elements in the form of a multiple thread cam located under the spherical joint and interacting with the vertical levers of the brackets of the light-optical elements interacting with the adjusting pins (patent of the Russian Federation No. 2149309, IPC F21V 14/02, F21V21/29, F21W131:205, published on May 20, 2000).

In the known technical solution, light emission control is performed by mechanical means ensuring the rotation of the light optical elements having a complex construction and large overall dimensions, reliability of which is reduced as the mechanical units wear out.

Technically, the most close to the claimed device is the surgical light comprising light-optical elements affixed to the body and hinged to each other, and light field control by mechanical means (application for EP No. 1568935, IPC F21S 8/00, F21S 2/00, published on Aug. 31, 2005).

The known lighting device features high illumination effectiveness. However, light emission control in the known lighting device is performed by mechanical means which ensure the rotation of the light-optical elements relative to each other, reliability of which is reduced as the mechanical parts wear out.

SUMMARY OF THE INVENTION

The object of the claimed invention is to increase the reliability of surgical lights whilst maintaining high illumination effectiveness and is attained as follows:

In the surgical light with the light emission control comprising light-optical elements affixed to the body and a light field adjustment device, according to the claimed technical solution, the light-optical elements are embodied in the form of main LEDs distributed over the light body surface and additional LEDs arranged between the main LEDs and having spatial orientation different from the spatial orientation of the main LEDs; the main and additional LEDs are arranged in groups so that the groups of main LEDs and the groups of additional LEDs are connected in between and with the light field adjustment device.

The main LEDs are affixed to the body of the lighting device wherein their optical axes cross the axis of the lighting device at the center of the light spot.

The additional LEDs are affixed to the body in such a way that their optical axes form a concentric ring-shaped light spot around the main spot.

Furthermore, the light field adjustment device includes a control unit, connected to which are groups of the main and additional LEDs by means of controls, each of which is connected to the power supply unit.

The arrangement of the main LEDs in a distributed manner on the body of the lighting device and of the additional LEDs between the main LEDs as well as grouping of the LEDs and different spatial orientations of the groups of main and additional LEDs enables electronic adjustment of the light spot diameter, which enhances the reliability of the lighting device.

The embodiment of the light field adjustment device as a device comprising a control unit, connected to which are the groups of main and additional LEDs by means of controls each of which is connected to the power supply unit, makes it possible to adjust the balance of currents flowing through the groups of main and additional LEDs, thus ensuring redistribution of the luminous flux inside the light field, i.e. enables electronic adjustment of the light field, thus enhancing the performance reliability of the lighting device.

The presence of essential features which are distinct from the prototype makes it possible to regard the claimed invention as novel.

No technical solutions have been revealed from the prior knowledge, which would coincide with the distinctive features of the claimed invention, therefore the claimed device meets the criterion of an inventive level.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
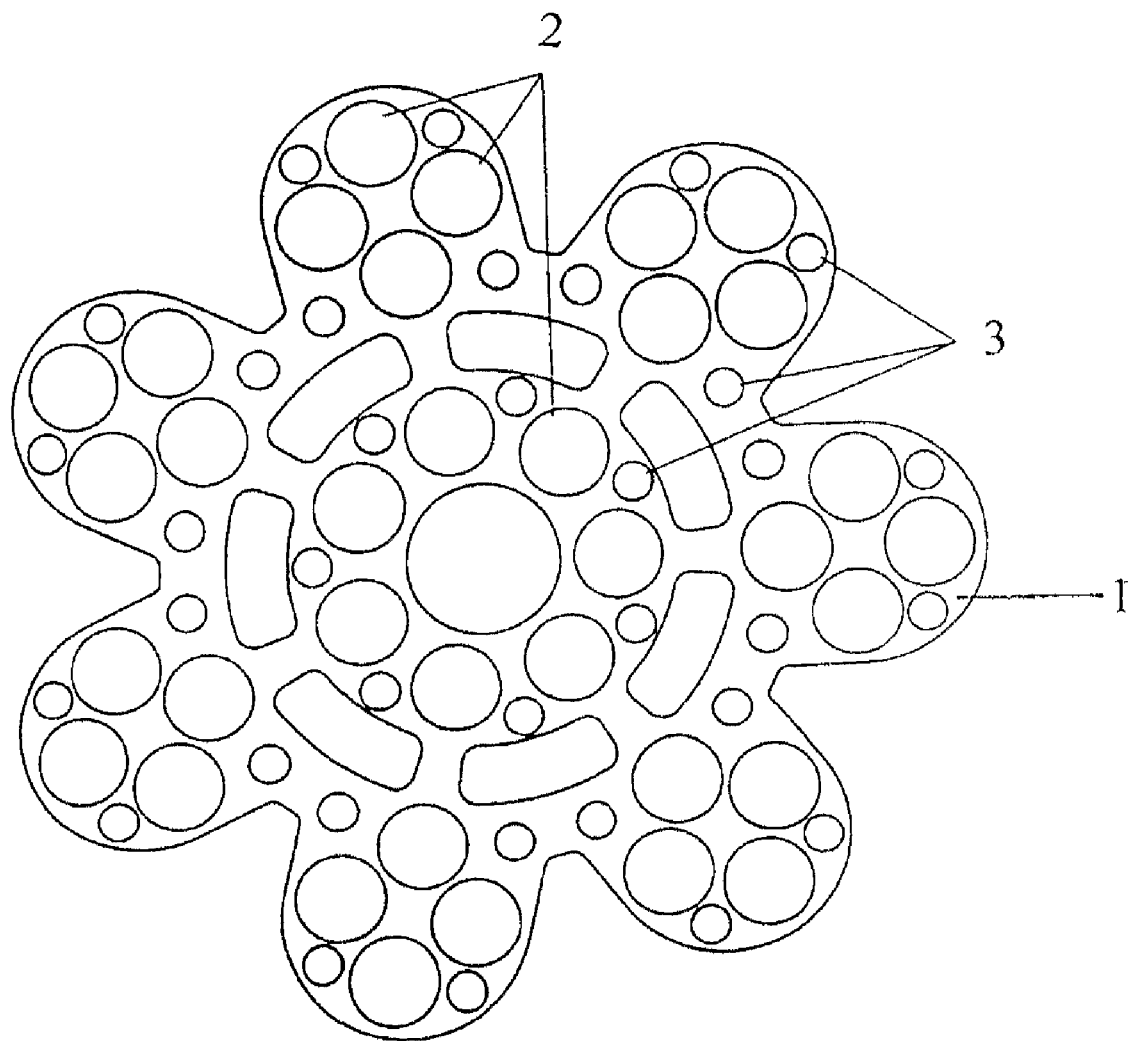
FIG. 1 is a diagram showing the arrangement of the main and additional LEDs on the surgical light.
Figure 2:
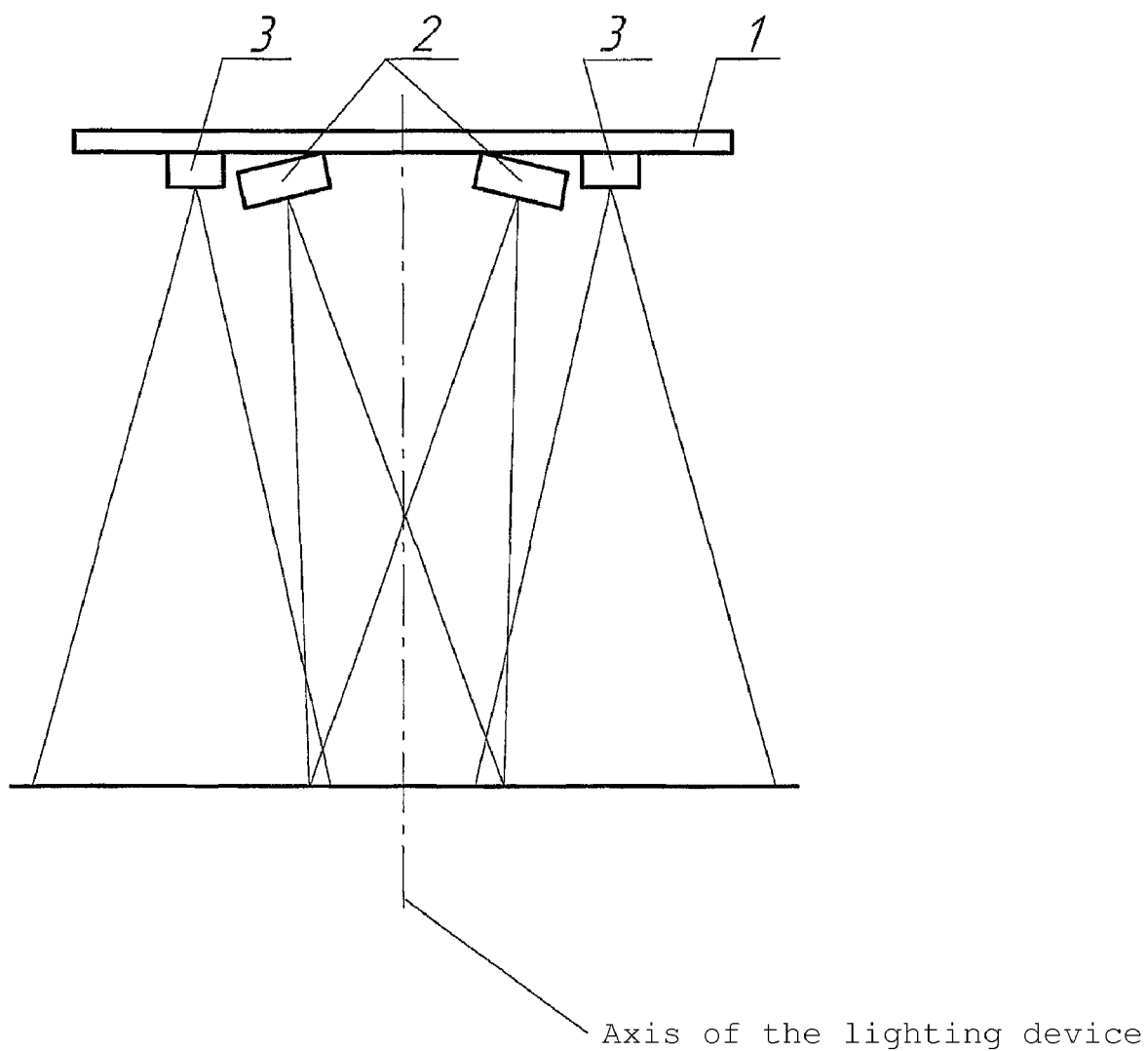
FIG. 2 shows the pathways of light rays in the lighting device.
Figure 3:
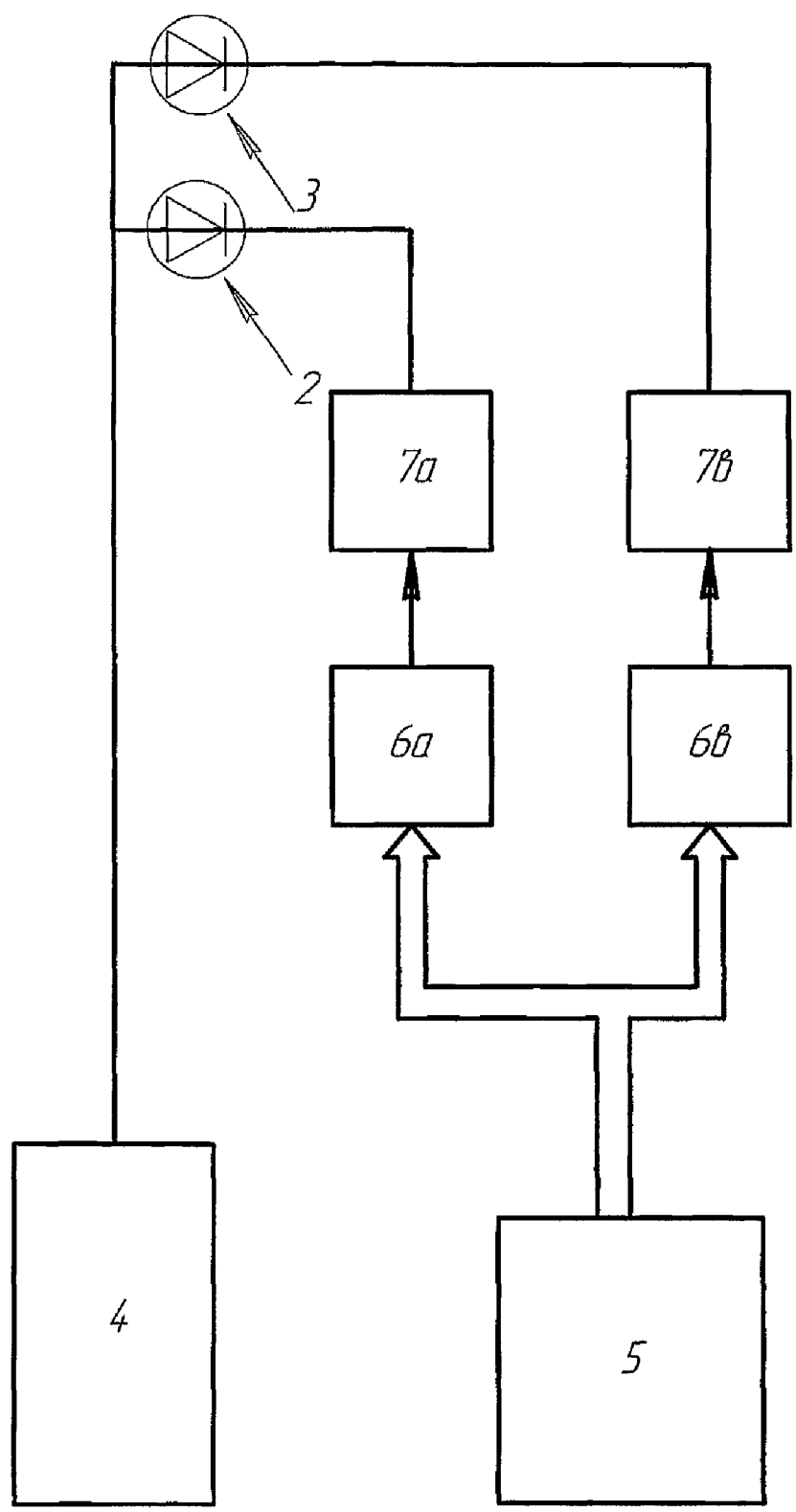
FIG. 3 is the light field control device of the surgical light.

Attached to body 1 of the lighting device are main LEDs 2 and additional LEDs 3 arranged in groups. Main LEDs 2 have a light beam width equal to 6.5° and are focused so that the optical axes thereof converge at the center of the light spot at a distance of 1 m from the surface. Additional LEDs 3 have a light beam width equal to 100 and are distributed between main LEDs 2 and the optical axes thereof form a concentric ring-shaped light spot around the main light spot with a radius equal to anything from 100 to 200 mm from the center of the spot, which is optimum for surgical lights. The light field control comprises power supply unit 4, control unit 5 with a microcomputer, digital-to-analog converters 6a and 6b, and current generators 7a and 7b.

As the lighting device is connected to the mains, the power from power supply unit 4 is concurrently fed to the groups of main LEDs 2 and additional LEDs 3. Where a larger area is to be illuminated (in case of extensive wounds) the groups of main LEDs 2 and additional LEDs 3 are switched on. In case of deep wounds where a light spot of smaller size is needed, only the groups of main LEDs 2 are switched on. For endoscopy, illumination is only needed for the zone where an operation is being performed with the help of an endoscope, therefore only the groups of additional LEDs 3 are switched on. In these cases the balance of currents flowing through the groups of main LEDs 2 and additional LEDs 3 is adjusted with the help of the microcontroller with control unit 5, digital-to-analog converters 6a and 6b and generators 7a and 7b, ensuring the redistribution of the luminous flux inside the light field.

While this invention has been particularly shown and described with references to preferred embodiments thereof, it will be understood by those skilled in the art that various changes in form and details may be made therein without departing from the scope of the invention encompassed by the appended claims.

What is claimed is:

1. A surgical light device having a device axis comprising:
    light-optical elements affixed to a body of the surgical light device; and
    a light field control unit;
    wherein the light-optical elements comprise:
        main LEDs spaced on a surface of the body so that optical axes of the main LEDs intersect the device axis at a center of a main light spot, and
        additional LEDs arranged between the main LEDs so that optical axes of the additional LEDs form a concentric ring-shaped light spot around the main light spot;
    wherein a spatial orientation of the additional LEDs is different from a spatial orientation of the main LEDs;
    wherein the main LEDs and additional LEDs form main LED groups and additional LED groups; and
    wherein the main LED groups and the additional LED groups are interconnected and connected with the light field control unit.

2. The surgical light device of claim 1 wherein the light field control unit comprises a control unit connected with the main LED groups and additional LED groups via controls, wherein each control is connected to a power supply unit.

* * * * *